(12) United States Patent
Moore (10) Patent No.: US 9,097,595 B2
(45) Date of Patent: Aug. 4, 2015

(54) SYSTEM AND METHOD FOR DETECTING AND MEASURING VIBRATION IN AN INDUSTRIAL ROLL

(75) Inventor: Robert Hunter Moore, Pittsburgh, PA (US)

(73) Assignee: Stowe Woodward, L.L.C., Middletown, VA (US)

(*) Notice: Subject to any disclaimer, the term of this patent is extended or adjusted under 35 U.S.C. 154(b) by 1450 days.

(21) Appl. No.: 12/577,389

(22) Filed: Oct. 12, 2009

(65) Prior Publication Data

US 2010/0125428 A1 May 20, 2010

Related U.S. Application Data

(60) Provisional application No. 61/114,604, filed on Nov. 14, 2008.

(51) Int. Cl.
*G01L 5/00* (2006.01)
*G01N 29/14* (2006.01)
*G01L 5/04* (2006.01)

(52) U.S. Cl.
CPC ............. *G01L 5/0085* (2013.01); *G01L 5/045* (2013.01); *G01N 29/14* (2013.01); *G01N 2291/2693* (2013.01)

(58) Field of Classification Search
CPC ........... G01N 29/14; G01N 2291/2693; G01L 5/045; G01L 5/0085
USPC .................................................. 702/34, 36, 56
See application file for complete search history.

(56) References Cited

U.S. PATENT DOCUMENTS

| 2,815,907 | A | 12/1957 | McCormick |
| 3,308,476 | A | 3/1967 | Kleesattel |
| 3,562,883 | A | 2/1971 | Kobayashi |
| 3,665,650 | A | 5/1972 | Przygocki |

(Continued)

FOREIGN PATENT DOCUMENTS

| CN | 1180163 A | 4/1998 |
| CN | 1782223 A | 6/2006 |

(Continued)

OTHER PUBLICATIONS

Office Action for Canadian Application 2,684,341 mailed on Jan. 18, 2012.

(Continued)

*Primary Examiner* — Mischita Henson
(74) *Attorney, Agent, or Firm* — Myers Bigel Sibley & Sajovec, PA (57) ABSTRACT

A system for determining the source of vibration of a nipped roll assembly includes: a first substantially cylindrical roll; a mating structure positioned relative to the first roll to form a nip therewith; a plurality of annular nip condition sensor units mounted on the first roll; each of the annular nip condition sensor units being positioned at different axial locations along the first roll and configured to provide nip condition signals from the nip, the signals indicating a nip condition at multiple circumferential locations; and a processor associated with the sensor units that receives signals from the sensor units. The processor is configured to convert the signals from the sensor units into nip condition readings for the multiple circumferential locations at each axial location. Such a system can detect irregularities in a roll or the mating structure that can cause undesired vibration.

9 Claims, 8 Drawing Sheets

(56) References Cited

U.S. PATENT DOCUMENTS

| | | | |
|---|---|---|---|
| 3,962,911 A | 6/1976 | Grenlund | |
| 4,016,756 A | 4/1977 | Kunkle | |
| 4,233,011 A | 11/1980 | Bolender et al. | |
| 4,352,481 A | 10/1982 | Forward | |
| 4,366,025 A | 12/1982 | Gordon, Jr. et al. | |
| 4,445,349 A | 5/1984 | Eibe | |
| 4,498,383 A | 2/1985 | Pav et al. | |
| 4,509,237 A | 4/1985 | Volz et al. | |
| 4,729,153 A | 3/1988 | Pav et al. | |
| 4,871,908 A | 10/1989 | Skuratovsky et al. | |
| 4,898,012 A | 2/1990 | Jones et al. | |
| 4,903,517 A | 2/1990 | Van Haag et al. | |
| 4,910,985 A | 3/1990 | Ballyns | |
| 4,938,045 A | 7/1990 | Rosenstock et al. | |
| 5,048,353 A | 9/1991 | Justus | |
| 5,086,220 A | 2/1992 | Berthold et al. | |
| 5,379,652 A | 1/1995 | Allonen | |
| 5,383,371 A | 1/1995 | Laitinen | |
| 5,466,343 A | 11/1995 | Kankaanpaa | |
| 5,562,027 A | 10/1996 | Moore et al. | |
| 5,592,875 A | 1/1997 | Moschel | |
| 5,614,676 A | 3/1997 | Dutt et al. | |
| 5,684,912 A | 11/1997 | Slaney et al. | |
| 5,699,729 A | 12/1997 | Moschel | |
| 5,739,626 A | 4/1998 | Kojima et al. | |
| 5,915,648 A | 6/1999 | Madrzak et al. | |
| 5,925,220 A | 7/1999 | Hirsch et al. | |
| 5,947,401 A | 9/1999 | Niccum | |
| 5,953,230 A | 9/1999 | Moore | |
| 6,284,103 B1 | 9/2001 | Eng et al. | |
| 6,341,522 B1 | 1/2002 | Goss et al. | |
| 6,354,013 B1 | 3/2002 | Mucke et al. | |
| 6,361,483 B1 | 3/2002 | Kirchner | |
| 6,387,214 B1 | 5/2002 | Kustermann | |
| 6,441,904 B1 | 8/2002 | Shakespeare | |
| 6,617,764 B2 | 9/2003 | Sebastian et al. | |
| 6,752,908 B2 | 6/2004 | Gustafson | |
| 6,892,563 B2 | 5/2005 | Gustafson et al. | |
| 6,910,376 B2 | 6/2005 | Maenpaa | |
| 6,981,935 B2 | 1/2006 | Gustafson | |
| 6,988,398 B2 | 1/2006 | Saloniemi et al. | |
| 7,185,537 B2 | 3/2007 | Muhs | |
| 7,225,688 B2 | 6/2007 | Moore et al. | |
| 2004/0053758 A1 | 3/2004 | Gustafson | |
| 2006/0090574 A1 | 5/2006 | Moore et al. | |
| 2006/0248723 A1 | 11/2006 | Gustafson | |
| 2007/0006644 A1 | 1/2007 | Schultheis | |

FOREIGN PATENT DOCUMENTS

| | | |
|---|---|---|
| CN | 1825082 A | 8/2006 |
| DE | 863 133 | 1/1953 |
| DE | 199 20 133 | 11/2000 |
| DE | 103 05 433 | 8/2004 |
| EP | 1 493 565 A2 | 1/2005 |
| EP | 1719836 A1 | 11/2006 |
| FR | 2 769 379 | 4/1999 |
| WO | WO 96/34262 | 10/1996 |
| WO | WO 98/49394 | 11/1998 |
| WO | WO 99/04181 | 1/1999 |
| WO | WO 01/53787 A1 | 7/2001 |
| WO | WO 02/086340 | 10/2002 |
| WO | WO 2004102141 A1 | 11/2004 |
| WO | WO 2004102141 A3 | 11/2004 |
| WO | WO 2007107625 A1 | 9/2007 |

OTHER PUBLICATIONS

Extended European Search Report corresponding to European Patent Application No. 09175910.0, Date of Mailing: Feb. 27, 2014, 6 pages.
Second Office Action for Chinese Application 200910222039.7 mailed on Feb. 22, 2012.
First Office Action from China Patent Office issued on May 25, 2011 for Patent Application No. 200910222039.7.
International Search Report and Written Opinion of the International Searching Authority for International patent application No. PCT/US2005/016456 mailed on Sep. 5, 2005.
A Study of Rubber Covered Press Nip Dynamics, James P. McNamee The Journal of the Technical Association of the Pulp and Paper Industry, vol. 48, No. 12, Dec. 1965, pp. 673-679.
Embedded Strain Gages for the Measurement of Strains in Rolling Contact, A. Bazergui and M. L. Meyer, Experimental Mechanics, Oct. 1968, pp. 433-441.
Experimental Investigation of Rolling Contact, Aris C. Spengos Journal of Applied Mechanics, Dec. 1965, pp. 859-864.
Knowles, S.F. et al; "Multiple microbending optical-fibre sensors for measurement of fuel quantity in aircraft fuel tanks;" vol. 68, No. 1-3 (Jun. 15, 1998) pp. 320-323. XP004139852.
McCollum, T et al; "Fiber optic microbend sensor for detection of dynamic fluid pressure at gear interfaces." vol. 65, No. 3, (Mar. 1, 1994) pp. 724-729 XP000435198.
Measurement of the Pressure-Time Profile in a Rolling Calendar Nip, Samuel F. Keller, 77th Annual Meeting of the Canadian Section of the Pulp and Paper Assn., 1991, pp. B89-B96.
Measurements of pressure distribution between metal and rubber covered rollers, G. J. Parish, British Journal of Applied Pyhsics, vol. 9, Apr. 1958, pp. 158-161.
Soft Calendar Nip: an interesting subject for research and Measurement, J. Koriseva et al., Paper and Timber, 73(1991):5 pp. 419-423.
Transducers and Techniques of Contact Pressure Measurement, Terry L. Merriman, The Society for Experimental Mechanics, Spring Conference, Jun. 1991, pp. 318-320.
European Search Report for EP 05 02 7237, dated Aug. 29, 2006.
PCT International Search Report PCT/US03/18895.
Anonymous: "Les Capteurs a Fibres Optiques Operationnels?" vol. 51, No. 13 (Oct. 20, 1986) pp. 49-51, 53, 55 XP002083807. (No Translation Available).
International Search Report for PCT/US01/02013.

SYSTEM AND METHOD FOR DETECTING AND MEASURING VIBRATION IN AN INDUSTRIAL ROLL

RELATED APPLICATION

This application claims priority from U.S. Provisional Patent Application No. 61/114,604, filed Nov. 14, 2008 and entitled System and Method for Detecting and Measuring Vibration in an Industrial Roll, the disclosure of which is hereby incorporated herein in its entirety.

FIELD OF THE INVENTION

The present invention relates generally to industrial rolls, and more particularly to industrial rolls with vibration measurement capability.

BACKGROUND OF THE INVENTION

Vibrations are commonly experienced in rotating machine components. In many cases, these vibrations can lead to product irregularities during manufacture, premature wear and failure of machine components, and unbearable environments. At the design level, the components are often sized so that their natural frequencies are well above the frequencies expected from vibration sources. To further reduce or prevent significant vibrations, balancing of individual components is often performed. Quite often, these preventative measures are insufficient at reducing the vibration levels to tolerable levels. Other techniques must be applied after the fact. In some corrective measures, damping is added to the components. With rotating machinery, the operational speeds are often adjusted to reduce certain frequencies of vibrations. In many cases, such measures are insufficient at controlling vibration, so more active techniques are required.

Paper machine rolls have specific challenges with vibrations. The rolls turn at certain rotational speeds, which will produce a level of vibration at the same frequency for any level of imbalance. Nipped rolls have additional challenges as follows:

1) Vibrations may occur at frequencies related to common multiples of roll diameters or felt length. For example, if one roll were three-fifths the diameter of its mating roll, there could be 15 locations on the larger roll where the same dot of the smaller roll touches. The larger roll could then vibrate at frequencies 15 times that of its rotational frequency. Felt seams of press felts often employed in paper machines have been blamed for inducing these types of vibrations and wear. This effect is sometimes called barring.
2) Other sources of wear can increase the levels of vibrations. If the nip is considered as a stiff spring, and the roll bodies as masses, this spring-mass system will typically vibrate at its natural frequency. If a roll vibrates at a frequency that is 15 times greater than its rotational frequency, fifteen worn or barred regions would be generated.
3) A paper sheet that is traveling into the nip may itself have irregularities, such as cyclical density, stiffness, or thickness variations. As such a sheet passes through the nip, the nip pressures will have a cyclical variation and vibrations may result. This source is often reported in calender stacks.
4) The roll could have beam bending vibrations.
5) Coatings on the rolls can be eccentric to the core or with the journal which causes vibrations at the same frequency as the roll rotation. Even when such a roll is dynamically balanced, the roll cover thickness variation causes a cyclical variation in the nip pressure. For example, if the cover is thickest at zero degrees and thinnest at 180 degrees, the rolls will deflect more at zero degrees than at 180 degrees. A vibration will result in addition to the pressure variation seen by the paper sheet.

Common reactions to excessive vibration levels include adjusting the operational speed, resurfacing the rolls, and changing the roll cover material. Changes to the operational speed are typically undesirable, since the other sections of the paper machine are optimized for a different speed; also, slower speeds reduce productivity and higher speeds may reduce quality. Resurfacing the rolls by regrinding the finish and final diameters usually involves substantial downtime and resurfacing costs. Roll covers having increased damping properties have also been developed to decrease the levels of vibrations; however, changing to a different cover material involves significant downtime to replace the rolls, and significant time and financial costs to replace the covering.

Present monitoring techniques usually involve placing vibration sensors at the bearing mounts and near the ends of the rolls. These sensors can pick up the major effects of the vibrations, but can not always pinpoint the source. It may be desirable to provide a vibration detection system that can generate more and better information about the vibrations of the roll.

SUMMARY OF THE INVENTION

As a first aspect, embodiments of the present invention are directed to a system for determining the source of vibration of a nipped roll assembly. The system comprises: a first substantially cylindrical roll; a mating structure positioned relative to the first roll to form a nip therewith; a plurality of annular nip condition sensor units mounted on the first roll; each of the annular nip condition sensor units being positioned at different axial locations along the first roll and configured to provide nip condition signals from the nip, the signals indicating a nip condition at multiple circumferential locations; and a processor associated with the sensor units that receives signals from the sensor units. The processor is configured to convert the signals from the sensor units into nip condition readings for the multiple circumferential locations at each axial location. In some embodiment, the nip condition sensor units are pressure sensors. Such a system can detect irregularities in a roll or the mating structure that can cause undesired vibration.

As a second aspect, embodiments of the present invention are directed to a method of assessing vibration in an industrial roll, comprising the steps of: providing a roll that includes a plurality of annular nip condition sensor units mounted thereon, each of the annular nip condition sensor units being positioned at different axial locations along the roll and configured to provide nip condition signals from a nip formed by the roll and a mating structure, rotating the roll; measuring a nip condition at multiple circumferential locations on each sensor unit; and determining the source of vibration in the roll based on the nip condition measurements.

DETAILED DESCRIPTION OF EMBODIMENTS OF THE INVENTION

The present invention will be described more particularly hereinafter with reference to the accompanying drawings. The invention is not intended to be limited to the illustrated embodiments; rather, these embodiments are intended to fully and completely disclose the invention to those skilled in this art. In the drawings, like numbers refer to like elements throughout. Thicknesses and dimensions of some components may be exaggerated for clarity.

Well-known functions or constructions may not be described in detail for brevity and/or clarity.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. As used herein, the term "and/or" includes any and all combinations of one or more of the associated listed items. Where used, the terms "attached", "connected", "interconnected", "contacting", "coupled", "mounted," "overlying" and the like can mean either direct or indirect attachment or contact between elements, unless stated otherwise.

Figure 1:
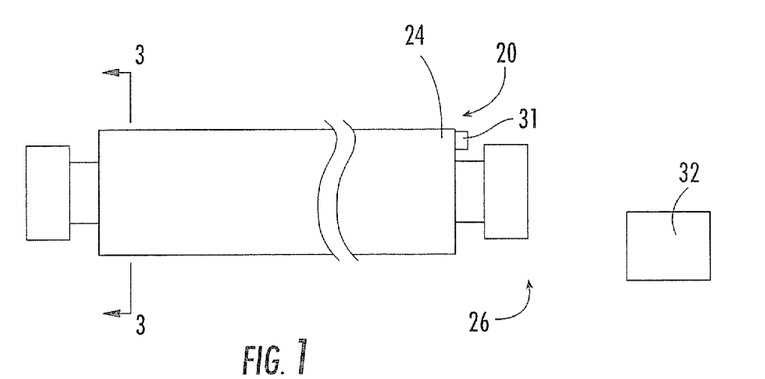
FIG. 1 is a schematic front view of a roll with a vibration detecting system according to embodiments of the present invention.
Figure 2:
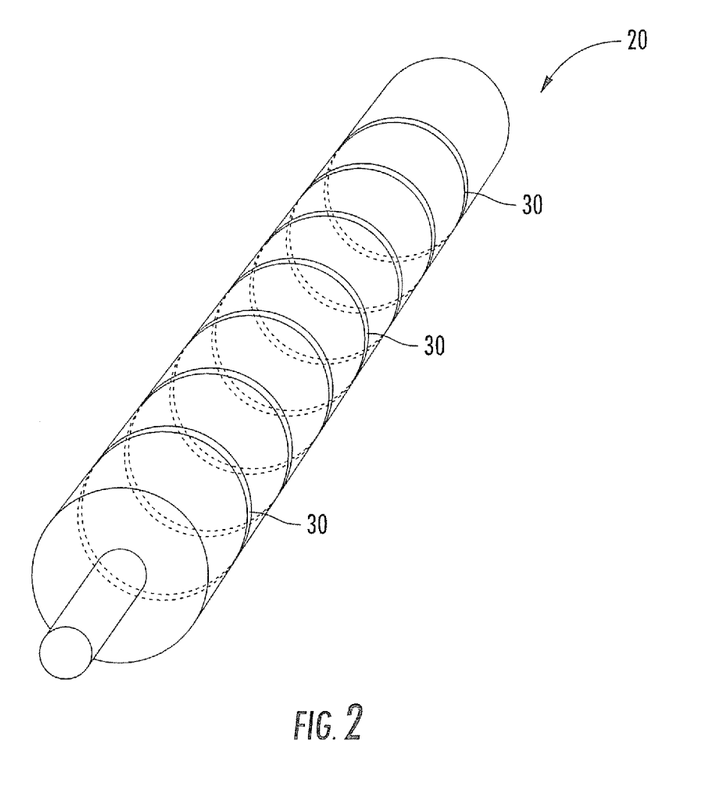
FIG. 2 is a perspective view of the roll of FIG. 1 with part of the cover removed to show the sensors of the vibration detecting system.
Figure 3:
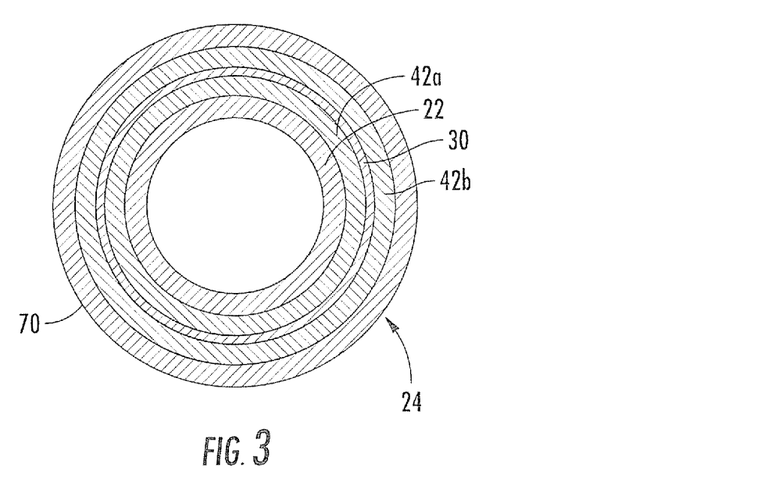
FIG. 3 is a section view of the roll of FIG. 1 taken along lines 3-3 thereof.

Referring now to the drawings, a roll, designated broadly at 20, is shown in FIGS. 1-3. The roll 20 is typically positioned adjacent to a mating structure, such as a mating roll or shoe of a shoe press, to form a nip through which a web can pass.

The roll 20 includes a hollow cylindrical shell or core 22 (see FIG. 3) and a cover 24 (typically formed of one or more polymeric materials) that encircles the core 22. The core 22 is typically formed of a corrosion-resistant metallic material, such as steel or cast iron. The core 22 can be solid or hollow, and if hollow may include devices that can vary pressure or roll profile.

The cover 24 can take any form and can be formed of any polymeric and/or elastomeric material recognized by those skilled in this art to be suitable for use with a roll. Exemplary materials include natural rubber, synthetic rubbers such as neoprene, styrene-butadiene (SBR), nitrile rubber, chlorosulfonated polyethylene ("CSPE"—also known under the trade name HYPALON), EDPM (the name given to an ethylene-propylene terpolymer formed of ethylene-propylene diene monomer), epoxy, and polyurethane. The cover 24 may also include reinforcing and filler materials, additives, and the like. Exemplary additional materials are discussed in U.S. Pat. No. 6,328,681 to Stephens, U.S. Pat. No. 6,375,602 to Jones, and U.S. Pat. No. 6,981,935 to Gustafson, the disclosures of each of which are hereby incorporated herein in their entireties.

Figure 4:
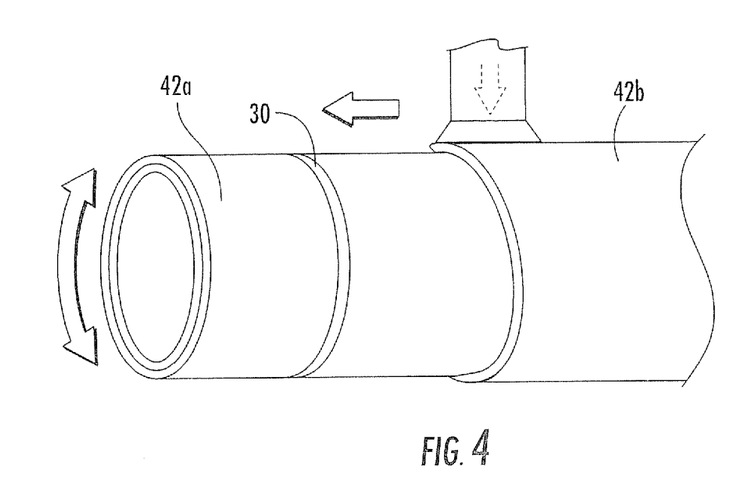
FIG. 4 is a perspective view of the outer base layer being applied over the inner base layer and sensors of the roll of FIG. 1.
Figure 5:
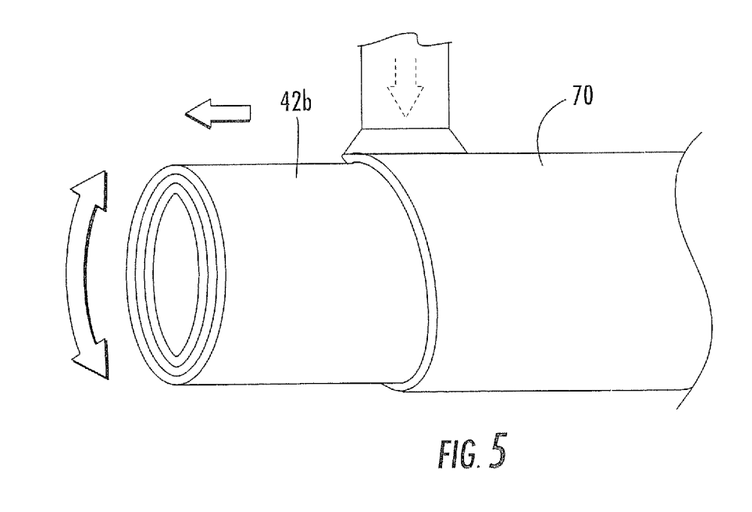
FIG. 5 is a perspective view of the topstock layer being applied over the outer base layer of FIG. 4.

In many instances, the cover 24 will comprise multiple layers. FIGS. 4 and 5 illustrate the application of an inner base layer 42a, an outer base layer 42b and a topstock layer 70; FIG. 3 shows these layers in cross-section. Additional layers, such as a "tie-in" layer between the outer base and topstock layers 42b, 70 and an adhesive layer between the shell 22 and the inner base layer 42a, may also be included.

Construction of the cover 24 may be carried out in any manner known to those skilled in this art to be suitable for the application of a roll cover. Exemplary methods are discussed in U.S. Patent Publication No. 2005/0261115, the disclosure of which is hereby incorporated herein in its entirety.

Referring now to FIGS. 1 and 2, a vibration sensing system 26 for sensing vibration in the roll 20 includes a plurality of nip condition sensors 30, each of which is embedded in the cover 24. As used herein, a sensor being "embedded" in the cover means that the sensor is entirely contained within the cover, and a sensor being "embedded" in a particular layer or set of layers of the cover means that the sensor is entirely contained within that layer or set of layers. The vibration sensing system 26 also includes a processor 32 and, in the illustrated embodiment, the sensors 30 are connected via electrical leads (not shown) to an electronics unit 31 that is mounted to one end of the roll 20. The electronics unit 31 is included to convert signals produced by the sensors 30 into easily-processed data; in some embodiments, each of the sensors 30 includes a transceiver that can transmit the signals wirelessly to the electronics unit 31 or to a remote receiver for processing (see, e.g., U.S. Pat. No. 7,392,715). The electronics unit 31 transmits the signals (typically wirelessly) to the processor 32 for subsequent processing and display.

Figure 9:
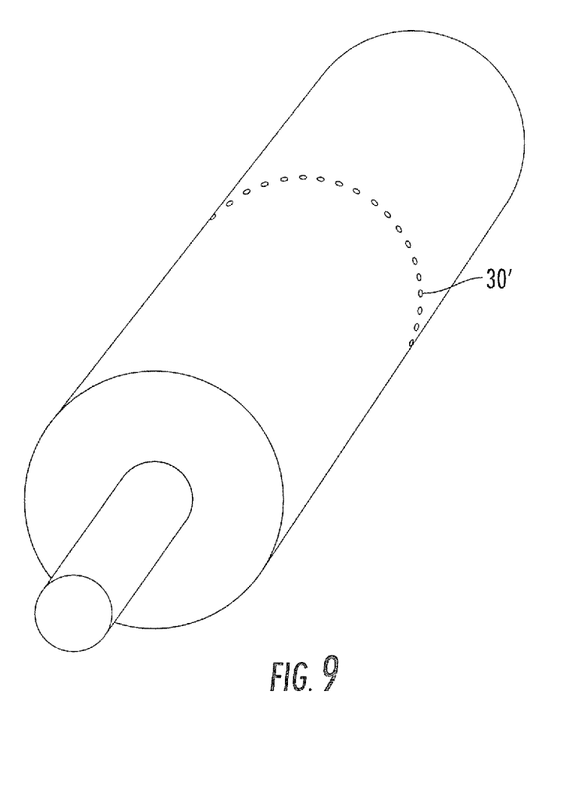
FIG. 9 is a schematic perspective view of a roll with a vibration detecting system according to additional embodiments of the present invention.

Referring still to FIG. 2, the arrangement of the sensors 30 of the sensing system 26 is shown therein. In the illustrated embodiment, the system 26 includes seven nip condition sensors 30 spaced generally equidistant from each other along the length of the roll 20, although typically more sensors 30 would be included at different axial locations to provide additional data. Each sensor 30 is annular and substantially encircles the roll 20 at one axial location. For the case of a continuous sensor 30 that wraps virtually 360 degrees around a roll, the pressure profile can be measured completely around the circumference of the roll 20. Alternatively, and as shown in FIG. 9, each continuous sensor 30 may be replaced by an annular ring of discrete, relatively closely spaced sensors 30'.

The sensors 30 measure a nip condition (typically pressure) either directly or indirectly. Any sensor that can measure pressure or another nip condition may be used. For example, the sensor 30 may directly measure pressure, displacement, proximity, strain, electrical charge, voltage, resistance, attenuation, capacitance or inductance, and this measurement can be correlated to nip pressure and/or nip width. Typical sensors include piezoelectric sensors, piezoceramic sensors, force sensitive resistor (FSR) sensors, resistive sensors, quantum tunneling composite (QTC) sensors, piezoresistive sensors, capacitive sensors, inductive sensors, optical fibers sensors, and EMFi film sensors. These sensor types are discussed below.

Piezoelectric sensors produce a charge or a voltage that is proportional to dynamic pressure. Suitable piezoelectric sensors can be obtained in the form of a cable from Measurement Specialties, Inc. (Valley Forge, Pa.). Kynar™ PVDF film may be used as a piezoelectric sensor and may also be obtained from Measurement Specialties, Inc.

Piezoceramic materials may be used at higher temperatures than the PDVF films. Material PSI-5A4E has a 350° C. Curie temperature. In many embodiments, these sensors would be arranged in a discrete array, as shown in FIG. 9. Exemplary sensors are available from Piezo Systems, Inc. Cambridge, Mass.

FSR sensors have a resistance that is nearly inversely proportional to pressure. FSR sensors may be obtained from Interlink Electronics, Inc. (Camarillo, Calif.) or from Tekscan, Inc. (South Boston, Mass.).

Resistive sensors include all sensors whose resistance is affected by the nip conditions. Very short strain gages may be oriented radially and would measure radial strain, which is closely related to radial pressure. Strain gages may be used to measure the circumferential strains in the nip. The axial strain may be near-zero away from the ends of the rolls, but could be non-zero if packaged to decouple the nearly plane strain conditions. These strains are related to pressure level, so strain gages are generally considered an indirect measurement method. Suitable strain gages may be obtained from Vishay Measurements Group (www.vishavmg.com) A QTC material is one for which resistance decreases as pressure is increased. QTC pills may be obtained from Peratech Ltd., Durham, United Kingdom.

Piezoresistive sensors also exhibit a coupling between resistance and applied stress or strain. These sensors could be oriented radially to measure radial pressure. An exemplary piezoresistive sensor is HSPPAR, available from Alps Electric Co., Ltd., Campbell, Calif.

Capacitive sensors measure pressure by measuring the change in capacitance between two plates or two objects. Capacitive pressure sensors can be obtained from Loadstar Sensors Inc., Sunnyvale, Calif.

Inductive sensors are commonly used for displacement measurements, which would be considered an indirect measurement. An exemplary inductive sensor is the 2402 sensor, available from Micro-Epsilon, Raleigh, N.C.

Optical fiber sensors have a number of available configurations. A microbead fiber may be wrapped around the circumference of the roll. This sensor is sensitive to radial strain. The change in strength/intensity of the light indicates the pressure or strain applied to the sensor. An exemplary device is shown in U.S. Pat. No. 6,429,421. An EFPI (extrinsic Fabry-Perot interferometric) sensor is a point sensor and acts as a highly sensitive displacement gauge. Several discrete EFPI sensors would be used in this case. Fiber Bragg grating sensors have a grating etched inside the fiber that acts to shift the wavelength of the light that passes through the sensor. In a typical application within a roll cover, the shift would indicate the level of circumferential strain in the cover material. Multi-mode and elliptical core (e-core) fibers will experience frequency shifts and intensity changes as the fiber is compressed.

EMFi films respond to pressure like an active capacitor. They may be suitable for low temperature and low pressure applications. Sensor material may be obtained from Emfit Ltd, Vaajakoski, Finland.

For many applications, temperature compensation may improve the accuracy of the sensor readings. Temperature compensation can be built into some of the sensor types. Separate temperature measuring sensors would be used for other sensors. Common temperature sensors include thermocouples, RTDs, and thermistors. Exemplary temperature compensation techniques are discussed in U.S. Patent Publication No. 2005/0278135, the disclosure of which is hereby incorporated herein in its entirety.

As discussed above, the sensors are annular and may be configured as either substantially continuous (as with sensors 30) or discrete (as with sensors 30'). A substantially continuous ring may have a gap between the start and stop positions in that it spans only a large part of the circumference, 355 degrees, for example. Such a gap can be used to help locate the position of a reading with the angular position. Alternately, a separate encoder or trigger can be used to keep the readings in sync with absolute position. For pure vibrations measurements, no synchronization may be needed. A gap also can help piezoelectric sensors remove the DC component of the signal.

The discrete sensors 30' shown in FIG. 9 may be used where it is convenient in terms of sensor availability or fabrication. For example, ceramic piezoelectric sensors may not be readily available in pre-made rings, so a sequence of sensors 30' may be used instead. The sensors 30' may be connected in parallel.

Although the sensors 30, 30' are illustrated as being located beneath the surface of the roll 20 embedded in the base layer 42, in other embodiments sensors may be located at the roll outside surface or beneath the surface at other depths, such as on top of the metal core, over the base, or over intermediate layers.

Figure 6:
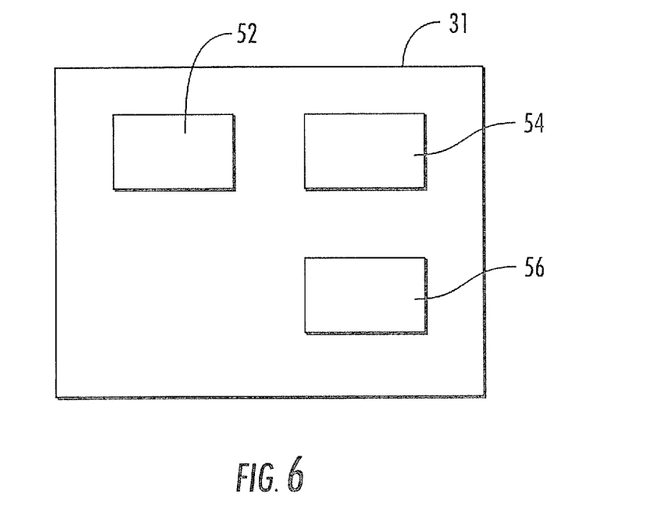
FIG. 6 is a schematic diagram of the electronics unit of the roll of FIG. 1.

Referring now to FIG. 6, the electronics unit 31 may include a signal conditioning module 52. Different sensors require different signal conditioning systems. For example, resistance sensors often have Wheatstone bridge circuitry. Other resistance-based circuits use a precision voltage or current source and measure the voltage over a known resistance element. Piezoelectric sensors typically use charge amplifiers. Capacitive sensors measure resonant frequencies or use a capacitance to voltage converter. Optical fiber sensors measure optical signal strength or frequency shifts. Thus, the signal conditioning module 52 converts the sensor output to a form that can be read by a data acquisition system 54 (below) or data logging system.

The electronics unit 31 may also include a data acquisition module 54. The data acquisition module 54 converts the sensor signal into a digital measurement. In many cases, the system uses an analog voltage to digital number (A/D) converter.

A controller 56 drives the sensors 30, the signal conditioning and data acquisition modules 52, 54 and any other electronics, and communicates wirelessly with the processor 32. The embedded controller 56 may shut down sections of the system at times to conserve power. The embedded controller 56 may also multiplex among the many available sensors 30.

The sensor measurements are communicated by the electronics unit 31 to the processor 32 at a location remote from the roll 20. The processor 32 converts the pressure signals into pressure readings for the multiple circumferential locations for each axially-located sensor. In many cases, this off-roll site is in an operator control room. The signal is typically transferred using RF communication. An exemplary RF transceiver is available from RF Monolithics, Inc., Dallas, Tex.

Other communication techniques are available. For example, the roll communication could be one-way in that signals are transmitted from the roll 20, but no communication is transmitted to the roll 20. Thus, the roll-based system would have a transmitter, and the off-roll site would use a receiver.

In some embodiments, IR communication and slip rings may also be used to communicate to and from the roll 20. Except for the mesh configuration discussed below, most of the electronics would be mounted on the head of the roll.

Another embodiment for communication is a wireless mesh configuration, where each sensor has a transceiver near its site, and the many sensors form a mesh configuration for communication. This approach is robust in that one weak site may reach a nearby site and have its information transmitted by a stronger wireless site. The robustness is also demonstrated when one site fails and the mesh reconfigures automatically to maintain the communication among the remaining sites. Wireless mesh products are available from Crossbow Technology, Inc. San Jose, Calif.

An arrangement of nip condition sensors such as discussed above would be especially helpful at pinpointing particular vibration problems, as discussed by the following examples.

Figure 7:
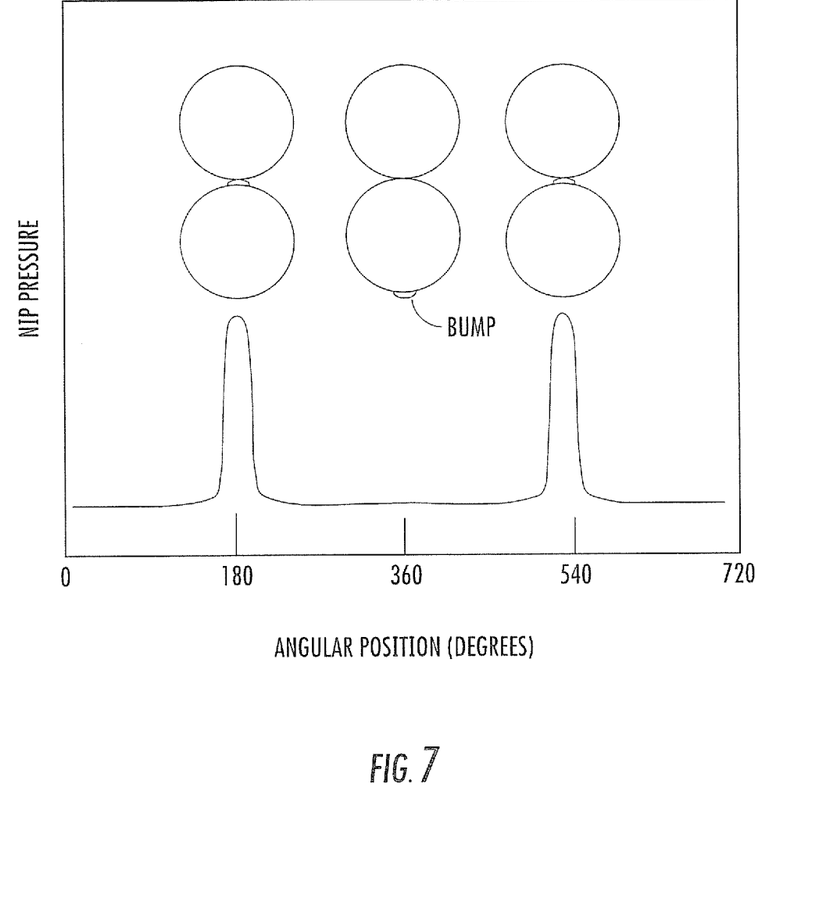
FIG. 7 is a graph plotting nip pressure as a function of nip angle to demonstrate how a roll surface bump that causes vibration can be detected.

In some instances one roll of a nipped pair has a flat spot or bump at its surface. As sensor readings are taken, the pressure profile would be fairly level until the region near the bump passes through the nip, as shown in FIG. 7. There would be one such bump during each revolution for the defective roll, and the mating roll would see one bump at a rotational period that is related to the ratios of the diameters of the rolls. As a result, the offending bump/flat spot can be identified and corrected.

Figure 8:
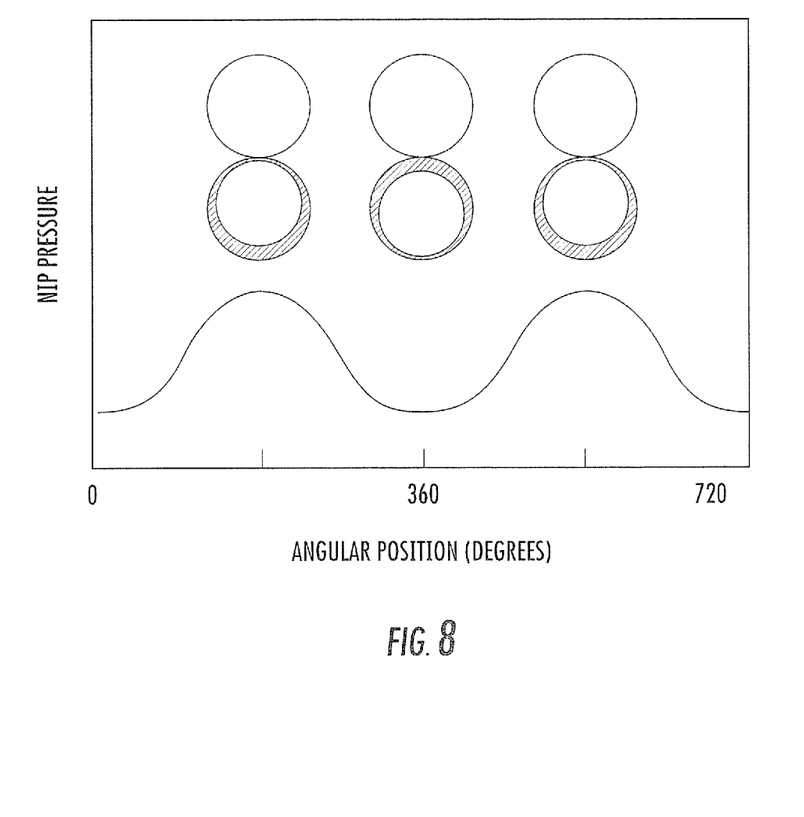
FIG. 8 is a graph plotting nip pressure as a function of nip angle to demonstrate how a non-concentric roll cover that causes vibration can be detected.

In other instances, a cover may be eccentric to its rotational axis. The outside diameter could be out of round, or the cover thickness could vary. After pressure readings are taken, a gently varying pressure profile would be seen for such a case, as is illustrated in FIG. 8. As before, the ratio of the rolls dictates the angular period if the mating roll is instrumented with sensors, rather than the eccentric roll. The regions with a thicker cover layer would act softer and have lower nip pressures than the thinner regions.

In either instance, the structure of the roll 20 may be adjusted (by grinding or the like) based on the pressure measurements to reduce vibration.

The above examples demonstrate that the machine-direction nip pressure is measured along with vibrations. Accelerometers output vibrations levels as a function of frequency and cannot distinguish between the two cases shown in FIGS. 7 and 8. Thus, the proposed sensing system can provide more pinpoint accuracy for the source of the problems. The system may also measure the magnitude of the direct effect of the vibrations on the paper product. That is, whereas an accelerometer can detect that significant vibrations are present, the proposed measurement system produces a measure of the direct effect of these vibrations on the nip pressure seen by the sheet. This direct approach can measure operational problems before the covers are worn or before damage or excessive vibrations develop.

The foregoing is illustrative of the present invention and is not to be construed as limiting thereof. Although exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. A method of assessing vibration in an industrial roll, comprising the steps of:
    providing a roll that includes a plurality of annular nip condition sensor units mounted thereon, each of the annular nip condition sensor units being positioned at different axial locations along the roll and configured to provide nip condition signals from a nip formed by the roll and a mating structure;
    rotating the roll;
    measuring a nip condition at multiple circumferential locations on each nip condition sensor unit; and
    determining the source of vibration in the roll based on the nip condition measurements.

2. The method defined in claim 1, further comprising the step of adjusting the structure of the roll based on the determining step.

3. The method defined in claim 1, wherein the mating structure is a second substantially cylindrical roll.

4. The method defined in claim 1, wherein the sensor units are substantially continuous annular sensors.

5. The method defined in claim 1, wherein the sensor units are multiple discrete sensors arranged in an annular pattern.

6. The method defined in claim 1, wherein the roll includes a polymeric cover, and wherein the sensor units are at least partially embedded in the cover.

7. The method defined in claim 6, wherein the polymeric cover is formed of a material selected from the group consisting of: natural rubber, neoprene, styrene-butadiene, nitrile rubber, chlorosulfonated polyethylene, EDPM, epoxy, and polyurethane.

8. The method defined in claim 1, wherein the nip condition sensor detects a condition selected from the group consisting of: pressure, displacement, proximity, strain, electrical charge, voltage, resistance, attenuation, capacitance and inductance.

9. The method defined in claim 8, wherein the nip condition sensor is a pressure sensor.

* * * * *

UNITED STATES PATENT AND TRADEMARK OFFICE
CERTIFICATE OF CORRECTION

PATENT NO. : 9,097,595 B2  
APPLICATION NO. : 12/577389  
DATED : August 4, 2015  
INVENTOR(S) : Robert Hunter Moore Page 1 of 1

It is certified that error appears in the above-identified patent and that said Letters Patent is hereby corrected as shown below:

Specification  
Column 5, Line 31: Please correct "(www.vishavmg.com)"  
to read -- (www.vishaymg.com). --

Signed and Sealed this  
Fifteenth Day of March, 2016

Michelle K. Lee  
*Director of the United States Patent and Trademark Office*